(12) United States Patent
Chandrasekar et al.

(10) Patent No.: US 8,262,599 B2
(45) Date of Patent: Sep. 11, 2012

(54) SPLINT COMPOSITION AND METHOD FOR USING SAME

(75) Inventors: N. R. Chandrasekar, Canton, MA (US); Donald McKay, Belmont, MA (US)

(73) Assignee: IQ Medical Devices, LLC, Bedford, MA (US)

( * ) Notice: Subject to any disclaimer, the term of this patent is extended or adjusted under 35 U.S.C. 154(b) by 497 days.

(21) Appl. No.: 12/421,463

(22) Filed: Apr. 9, 2009

(65) Prior Publication Data

US 2010/0262057 A1    Oct. 14, 2010

(51) Int. Cl.
*A61F 5/00*    (2006.01)

(52) U.S. Cl. ............... 602/20; 602/21; 602/22

(58) Field of Classification Search ........... 602/20–22; 128/878–880
See application file for complete search history.

(56) References Cited

U.S. PATENT DOCUMENTS

| | | |
|---|---|---|
| 4,441,489 A | 4/1984 | Evans et al. |
| 4,644,941 A * | 2/1987 | Ogle, II ............... 602/22 |
| 4,932,396 A | 6/1990 | Garris |
| 5,947,915 A | 9/1999 | Thibodo, Jr. |
| 6,932,782 B2 * | 8/2005 | Ferraioli ............... 602/22 |
| 7,169,121 B2 * | 1/2007 | Berrehail ............... 602/22 |
| 2005/0027223 A1 | 2/2005 | Nguyen |
| 2011/0144553 A1 * | 6/2011 | Barnes ............... 602/22 |

FOREIGN PATENT DOCUMENTS

| | | |
|---|---|---|
| JP | 63-186429 | 11/1988 |
| JP | 2002-011037 | 1/2002 |
| KR | 20-0444034 | 4/2009 |

OTHER PUBLICATIONS

International Preliminary Report on Patentability for International Application No. PCT/US2010/030608, dated Oct. 20, 2011.
International Search Report for International Application PCT/US2010/030608, dated Mar. 8, 2011.

* cited by examiner

*Primary Examiner* — Michael A. Brown
(74) *Attorney, Agent, or Firm* — Morse, Barnes-Brown & Pendleton, P.C.; Lisa M. Treannie, Esq.

(57) ABSTRACT

Disclosed herein is a splint for splinting a digit, preferably a finger, thumb or toe, rings for use in a splint, dorsal bars for use in the splint, a method for splinting a digit using the splint described herein, and a kit comprising components of the splint and, optionally, related items such as one or more ring sizers, cutting tools, adhesive, etc.

5 Claims, 16 Drawing Sheets

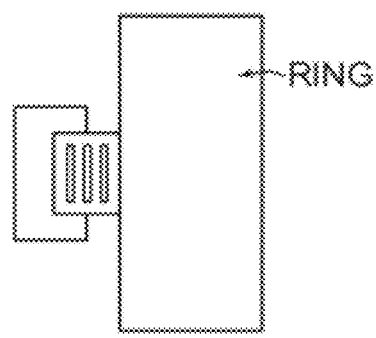
FIG. 15
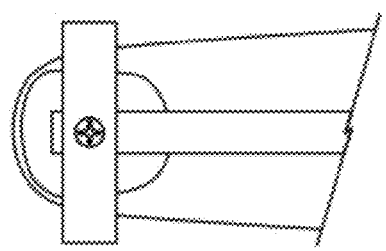
FIG. 16
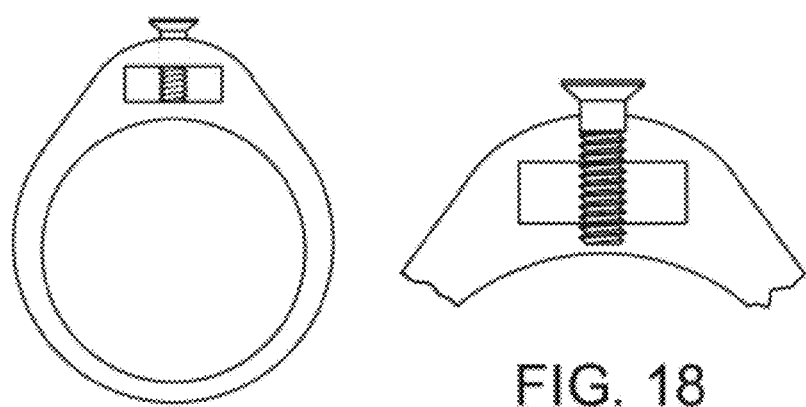
FIG. 17
FIG. 18

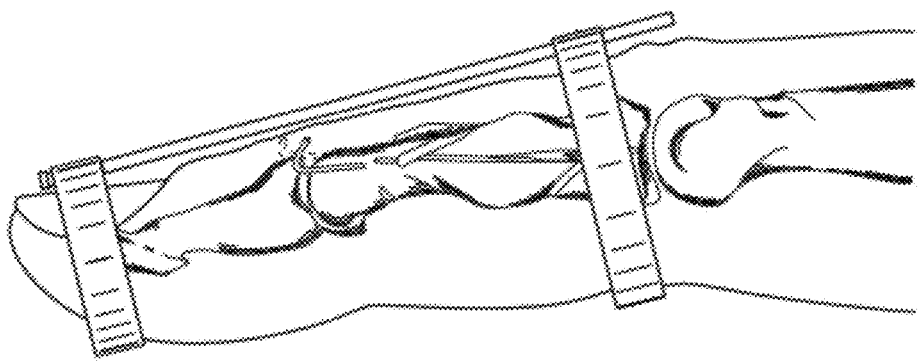
FIG. 30
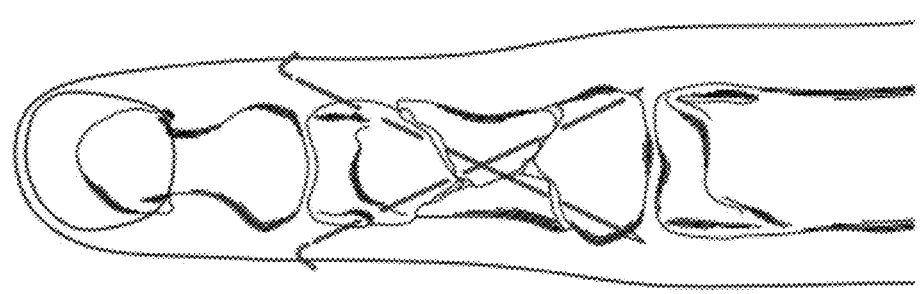
FIG. 31
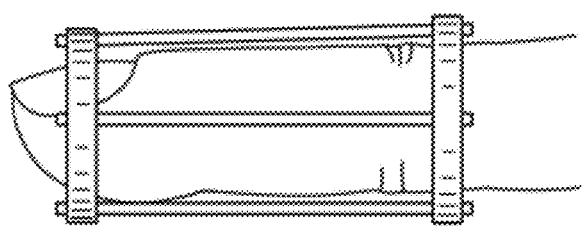 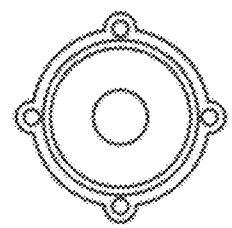
FIG. 32                    FIG. 33

SPLINT COMPOSITION AND METHOD FOR USING SAME

BACKGROUND OF THE INVENTION

Mallet finger is a commonly used term in medical practice for a closed rupture of the extensor tendon at the distal interphalangeal joint of a finger (FIG. 1). Mallet finger is frequently a result of a trivial injury and is usually minimally painful. The injury is typically caused by forced flexion of the distal interphalangeal joint of a finger, resulting in stretching and rupture of the extensor tendon, usually at or near its insertion on the dorsal lip of the distal phalanx. On examination patients have a characteristic flexion deformity of the finger at the distal interphalangeal joint (FIGS. 2-5). X-rays are usually negative, although on occasion there may be a small fracture of the distal phalanx in the location of the tendon's insertion, indicating that the extensor tendon over the joint has pulled off a piece of bone.

A splint typically needs to be worn for a minimum of six weeks (continuously, without removal or change) for healing of the tendon to occur. Multiple splint mechanisms have been developed to treat mallet finger, including stack splints, oval 8 splints, and simple alumina foam splints. Existing splint solutions are largely unsatisfactory for several reasons. First, they require that the finger stay dry, precluding washing or showering unless a watertight "bag" is worn over the area. If moisture accumulates under the splint, problems can arise with maceration of the skin under the splint. Second, if the fit of the splint is too loose, the finger will have a persisting flexion deformity at the distal interphalangeal joint, resulting in treatment failure. Moreover, even a well performed splint change during the course of treatment may disrupt the healing process if even a small amount of flexion occurs, setting treatment back substantially. Surgery may not be effective for treating a mallet finger injury and increases the potential for complications; in addition, even surgical treatment is usually combined with splinting.

Current splint solutions frequently fall off, become loose, may cause pressure sores or skin maceration, and interfere with daily activities and personal hygiene. Accordingly, new treatment modalities are needed to solve one or more of these problems and to effectively treat a mallet finger injury or other injury to tendon, ligament and/or bone in a digit (e.g., a boutonniere deformity, a volar plate fracture or dislocation, a fracture of the middle phalanx, fracture of the proximal phalanx of the thumb).

SUMMARY OF THE INVENTION

Disclosed herein is a splint for splinting a digit, preferably a finger, thumb or toe, rings for use in a splint, dorsal bars for use in the splint, a method for splinting a digit using the splint described herein, and a kit comprising components of the splint and, optionally, related items such as one or more ring sizers, cutting tools, adhesive, etc. Preferred splints of the invention can be worn for 6-8 weeks without complications and allow the patient to shower, wash his hands and carry on most daily activities. Preferred splints do not have odor problems, are not unsightly, and remain firmly attached without compromising circulation or causing pressure problems vis-à-vis the skin. The splints of the invention may decrease the frequency and number of office visits for follow up.

In one embodiment the invention relates to a splint for splinting a digit comprising: a dorsal bar having two ends; a distal ring comprising a portion adapted to securely connect to one end of the dorsal bar; and a proximal ring comprising a portion adapted to securely connect to the other end of the dorsal bar, wherein the dorsal bar is securely connected to both the distal and proximal rings such that one or more joints of a digit to which the splint is applied is maintained in an extended position. In a preferred embodiment the distal ring further comprises a portion adapted to secure the distal ring to a fingernail. In preferred embodiments the distal and proximal rings are of suitable size and shape to be worn or fitted on a digit.

The invention also relates to a splint for splinting a digit comprising a dorsal bar having two ends; a distal ring comprising one or more portions adapted to securely connect to one end of the dorsal bar; and a proximal ring comprising one or more portions adapted to securely connect to the other end of the dorsal bar, wherein the dorsal bar is securely connected to both the distal and proximal rings such that one or more joints of a digit to which the splint is applied is maintained in an extended position. In one embodiment the distal ring further comprises a portion adapted to secure the distal ring to a fingernail. In one embodiment the portion of the distal ring adapted to secure the distal ring to a fingernail comprises a portion suitable for receiving an adhesive. In one embodiment one or more portions of the distal ring, the proximal ring, or both the distal and proximal rings adapted to securely connect to the dorsal bar are adapted to engage the dorsal bar. In one embodiment one or more portions of the distal ring, the proximal ring, or both the distal and proximal rings adapted to securely connect to the dorsal bar comprises a housing having a hollow slot therethrough suitable to receive the dorsal bar. In one embodiment one or more portions of the distal ring, the proximal ring, or both the distal and proximal rings adapted to securely connect to the dorsal bar comprises a ratchet capable of engaging the dorsal bar. In one embodiment the dorsal bar comprises an integrated gear rack which engages the ratchet.

In another embodiment the dorsal bar comprises one or more (e.g., multiple) spaced transverse striations which frictionally engage one or more portions of the distal ring, the proximal ring, or both the distal and proximal rings adapted to securely connect to the dorsal bar. In another embodiment the dorsal bar comprises one or more (e.g., multiple) spaced beads or bumps which frictionally engage one or more portions of the distal ring, the proximal ring or both the distal and proximal rings adapted to securely connect to the dorsal bar. In another embodiment the dorsal bar comprises one or more holes or slots which engage a connector in one or more portions of the distal ring, the proximal ring or both the distal and proximal rings adapted to securely connect to the dorsal bar. In one embodiment the connector is a screw, a snap, or a rivet.

In one aspect the dorsal bar slidably engages with both the proximal and distal rings. In another aspect the dorsal bar slidably engages with both the proximal and distal rings in only one direction. In one embodiment the dorsal bar comprises a stopping mechanism.

The inventions also relates to a ring of suitable size and shape to be fitted on a digit comprising one or more portions adapted to securely connect to one end of the dorsal bar. In one embodiment one or more portions of the ring adapted to securely connect to the dorsal bar are adapted to engage the dorsal bar. In one embodiment one or more portions of the ring adapted to securely connect to the dorsal bar comprises a housing having a hollow slot therethrough suitable to receive the dorsal bar. In one embodiment one or more portions of the ring adapted to securely connect to the dorsal bar comprises a ratchet capable of engaging the dorsal bar. In one embodiment the ring further comprises a portion adapted to secure the ring to a fingernail.

The invention also relates to a dorsal bar having a distal and a proximal end and adapted to engage a ring at each of the distal and proximal ends to form a splint. In one embodiment the dorsal bar comprises one or more spaced transverse striations capable of frictionally engaging a ring. In another embodiment the dorsal bar comprises one or more beads or bumps capable of frictionally engaging a ring. In another embodiment the dorsal bar comprises one or more holes or slots capable of engaging a connector in a ring.

The invention also relates to a method of splinting a finger comprising selecting a proximal ring of an appropriate size, wherein the proximal ring comprises a portion adapted to securely connect to one end of a dorsal bar; selecting a distal ring of an appropriate size, wherein the distal ring comprises a portion adapted to securely connect to one end of a dorsal bar; fitting the proximal and distal rings to a digit to be splinted; and securely connecting a dorsal bar to both the distal and proximal rings such that one or more joints of the digit to which the splint is applied is maintained in an extended position. In one embodiment of the method the distal ring further comprises a portion adapted to secure the ring to a fingernail, and wherein the method further comprises securing the distal ring to the fingernail of the digit to which the splint is applied.

The invention also relates to a kit comprising one or more components selected from the group consisting of one or more dorsal bars; one or more distal rings comprising a portion adapted to securely connect to one end of the dorsal bar; and one or more proximal rings comprising a portion adapted to securely connect to the other end of the dorsal bar. In one embodiment the distal ring further comprises a portion adapted to secure the ring to a fingernail. In one embodiment the kit comprises at least one dorsal bar, at least one distal ring, and at least one proximal ring. In one embodiment the kit further comprising one or more components selected from the group consisting of one or more ring sizers, a cutting tool, adhesive, adhesive remover, and instructions for use.

It should be understood that embodiments of the invention may be freely combined with one another, and such combinations are within the scope of the invention.

BRIEF DESCRIPTION OF THE DRAWINGS

FIG. 15 shows a side view of a dorsal bar having a stopping mechanism; the dorsal bar is engaged by a ring of the invention.

FIG. 16 illustrates one embodiment of the dorsal bar engaged with a proximal ring. In this embodiment a screw or other fastener passes through a hole or slot in the ring and fixedly connects (e.g., by screwing) to the dorsal bar (e.g., to a hole or slot in the dorsal bar).

FIG. 17 shows another view of the embodiment of FIG. 16.

FIG. 18 shows a transparent view of the screw fixation aspect of the embodiment of FIG. 16.

FIG. 30 illustrates a side view of one embodiment of a splint of the invention applied to a finger with a fracture of the middle phalanx.

FIG. 31 shows a top view of a finger with a fracture of the middle phalanx.

FIG. 32 shows one embodiment of a splint of the invention comprising a distal ring, a proximal ring, and multiple dorsal bars. Each ring is adapted to engage more than one (multiple) dorsal bars.

FIG. 33 shows a cross-sectional view looking inward from the finger tip of one embodiment of a splint of the invention; shown is a distal or proximal ring engaged with four dorsal bars.

FIG. 37 illustrates a splint assembly comprising such a dorsal bar engaged with proximal and distal rings.

FIG. 39 illustrates a splint assembly comprising such a dorsal bar engaged with proximal and distal rings.

DETAILED DESCRIPTION OF THE INVENTION

Disclosed herein is a splint for splinting a digit, preferably a finger, thumb or toe, rings for use in a splint, dorsal bars for use in the splint, a method for splinting a digit using the splint described herein, and a kit comprising components of the splint and, optionally, related items such as one or more ring sizers, cutting tools, adhesive, etc.

As described herein, a splint according to the invention is comprised of at least 3 parts or components: a distal ring, a proximal ring, and a dorsal bar.

It should be understood that although the splint is described herein extensively with respect to splinting of mallet finger injury, the splint is equally useful with other injuries of the fingers, thumbs, and toes (FIGS. 26-29 and 30-31). The positioning of one or more of the proximal ring, distal ring or dorsal bar may, accordingly, be different from that described for mallet finger injury. However in principle the operation of the splint remains the same. One or more dorsal bars span one or more joints to immobilize the joint(s), and the dorsal bar(s) is secured on one end to a proximal ring and on the other end to a distal ring. The distal ring is positioned on the finger, toe or thumb distal to the joint(s) to be immobilized, and the proximal ring is positioned proximal to the joint(s) to be immobilized. For example, the splint can be used to immobilize a finger at the proximal interphalangeal joint for both a boutonierre deformity and volar plate fracture or dislocation (preferably utilizing two dorsal bars for the volar plate fracture or dislocation).

In some embodiments the distal ring will be secured to the fingernail or toenail of the digit, e.g., with an adhesive. In other embodiments, such as embodiments in which the distal ring is not positioned across the nail, the distal ring will not be secured to the nail. Proper fitting will minimize undesired movement of the rings or splint.

The invention encompasses a ring for use in a splint as described herein. Rings according to the invention are of suitable size and shape to be worn or fitted on a finger, thumb, or toe and are adapted to securely engage one or more dorsal bars to form a splint assembly. In one embodiment the ring comprises one or more portions adapted to receive and engage one or more dorsal bars. In one embodiment the ring comprises a housing having one or more hollow paths or slots therethrough suitable for receiving and engaging one or more dorsal bars. In some embodiments the ring is further configured to be securely attached to a nail surface. For example, the ring can comprise a portion which is suitable for receiving an adhesive substance and being fixedly secured to a nail surface. The invention also relates to a dorsal bar having a distal and a proximal end and adapted to engage a ring at each of the distal and proximal ends as described further herein.

Figure 7:
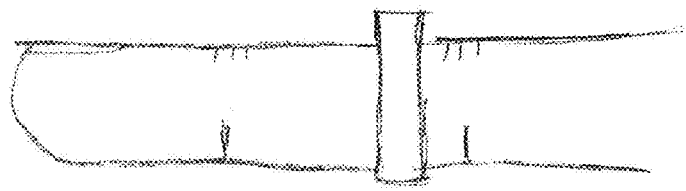
FIG. 7 shows a proximal ring embodiment positioned on a finger.

In use of the splint for mallet finger injury, the proximal ring is selected to fit around the diameter of the mid-portion of the middle phalanx of the digit to be splinted (FIG. 7). The distal ring is selected to fit around the diameter of the distal phalanx such that the ring is positioned across the nail (e.g., finger nail) of the digit to be splinted (FIG. 9), and is firmly (securely) attached to the nail. The dorsal bar is connected to both the distal and proximal rings and positioned such that it holds the distal interphalangeal joint in full extension.

The splint described herein allows for improved hygiene of a wearer in comparison with existing splints; the splint is not impacted by exposure to water, thus allowing for normal bathing and washing of the injured area. In addition, the described splint reduces the surface area over which the splint contacts the skin of the wearer, thereby reducing the likelihood of maceration and other undesirable effects. It should be noted that although the invention is described herein extensively with regard to a finger (including a thumb) as the digit to be splinted, the splint can be used to splint a toe as well.

The distal and proximal rings can be formed of any material or combination of materials as long as the resulting ring is sufficiently rigid to prevent undesirable stretching or bending under normal conditions during the duration of use. Undesirable stretching or bending in the context of mallet finger injury is stretching or bending which permits the interphalangeal joint to assume a position short of full extension. In other treatment contexts, undesirable stretching or bending is that which permits the immobilized joint(s) to assume a position which is inconsistent with treatment. The rings can be solid or can comprise perforations to allow for airflow, provided that the perforations do not compromise the structural integrity of the rings and permit undesirable stretching or bending.

For example, the rings can be formed of plastic or other polymer, metal (e.g., stainless steel), glass, and the like. In a preferred embodiment the rings are formed of a water-resistant or waterproof material and may be solid or porous. In one embodiment the rings can be radiolucent, translucent or transparent. In a preferred embodiment the rings are formed of a non-reactive material, i.e., a material which does not react with the skin; preferably the material does not cause a local skin inflammation (e.g., contact dermatitis).

Each of the rings may be fixed or adjustable in size (internal diameter), provided that such adjustability does not permit undesirable stretching or bending of the ring once an appropriate size is determined and the ring is fixed at that size and placed on the wearer's finger. The width and thickness of each ring will depend upon the physical properties of the material from which it is formed in that the combination of the material used and the width and thickness of the ring must provide sufficient rigidity. Generally each ring may be from about $1/8^{th}$ of an inch to $1/4^{th}$ of an inch wide and approximately $1/8^{th}$ an inch in thickness; the ring may be uniform in its dimensions, or certain parts may be thicker than others (e.g., the upper part of the ring housing the bar and/or the disk). However, these parameters may be varied depending on the structural or physical properties of the material from which the ring is formed. For example, rings made of very strong or rigid material may be less than an eighth of an inch thick and an eighth of an inch wide, while rings made of weaker material may be more than an eighth of an inch thick and a quarter of an inch wide, in order to achieve sufficient rigidity.

In some embodiments one or more of the rings and/or the dorsal bar may be decorated or adorned to look like jewelry. For example, one or more of the rings and/or dorsal bar may be colored, e.g., by painting, dyeing or a process which imparts color variably or uniformly to the material from which the item is fabricated. One or more of the rings and/or the dorsal bar may also be adorned with sequins, beads, simulated gemstones and the like to improve or embellish the appearance on the wearer.

Figures 8, 9:
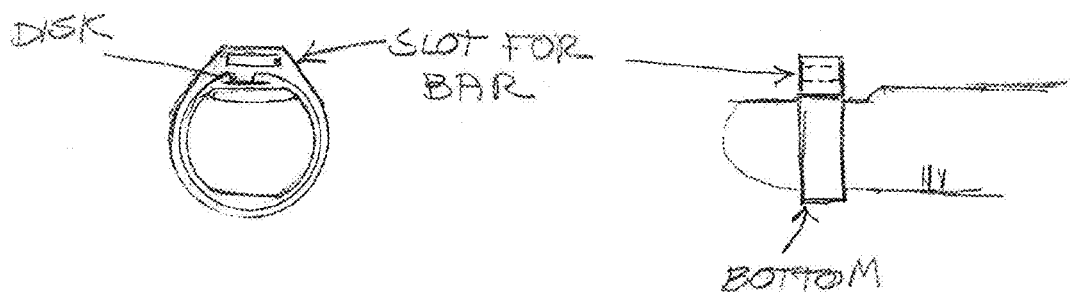
FIG. 8 shows one embodiment of a distal ring having a housing in which a flattened disk is affixed to the inner surface of the ring or housing for attaching the ring to the finger nail.
FIG. 9 shows a side view of a distal ring having a housing for the dorsal bar which has a hollow path or slot through it.
Figure 10:
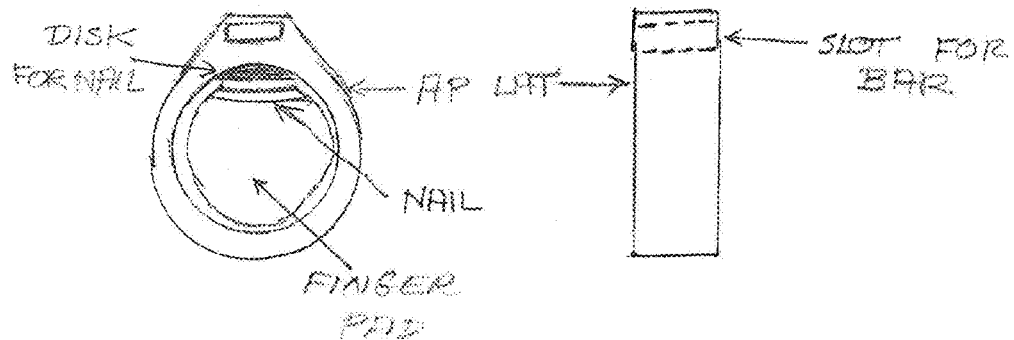
FIG. 10 illustrates one embodiment of a distal ring having a housing for the dorsal bar which has a hollow path or slot through it and a flattened disk is affixed to the inner surface of the ring or housing for attaching the ring to the finger nail. The view point is from the tip of the finger.

The distal ring is configured to be securely attached to the nail surface of the finger to be splinted. The distal ring has a portion which is generally flat and suitable for receiving an adhesive substance (FIGS. 8 and 10). The generally flat portion of the ring can be a flattened portion of the ring itself or can be an additional portion attached to the ring. In either case, the flattened portion resides on the inside of the distal ring to allow the flattened portion to contact the nail of the wearer when the ring is fitted to the finger to be splinted. By way of example only, the flattened portion of the distal ring can be a small circular element (e.g., a disk), attached on the inside of the ring, which measures $1/8^{th}$ of an inch to $3/8^{th}$ of an inch in diameter. The flattened portion may be adjacent to (ventral to) the portion of the ring adapted to receive the dorsal bar as discussed below. For example, the flattened portion can be adjacent to or attached to the dorsal bar housing on the ring. The flattened portion need not be circular but rather can be of any size and shape suitable to adhere the ring to the fingernail.

Figure 1:
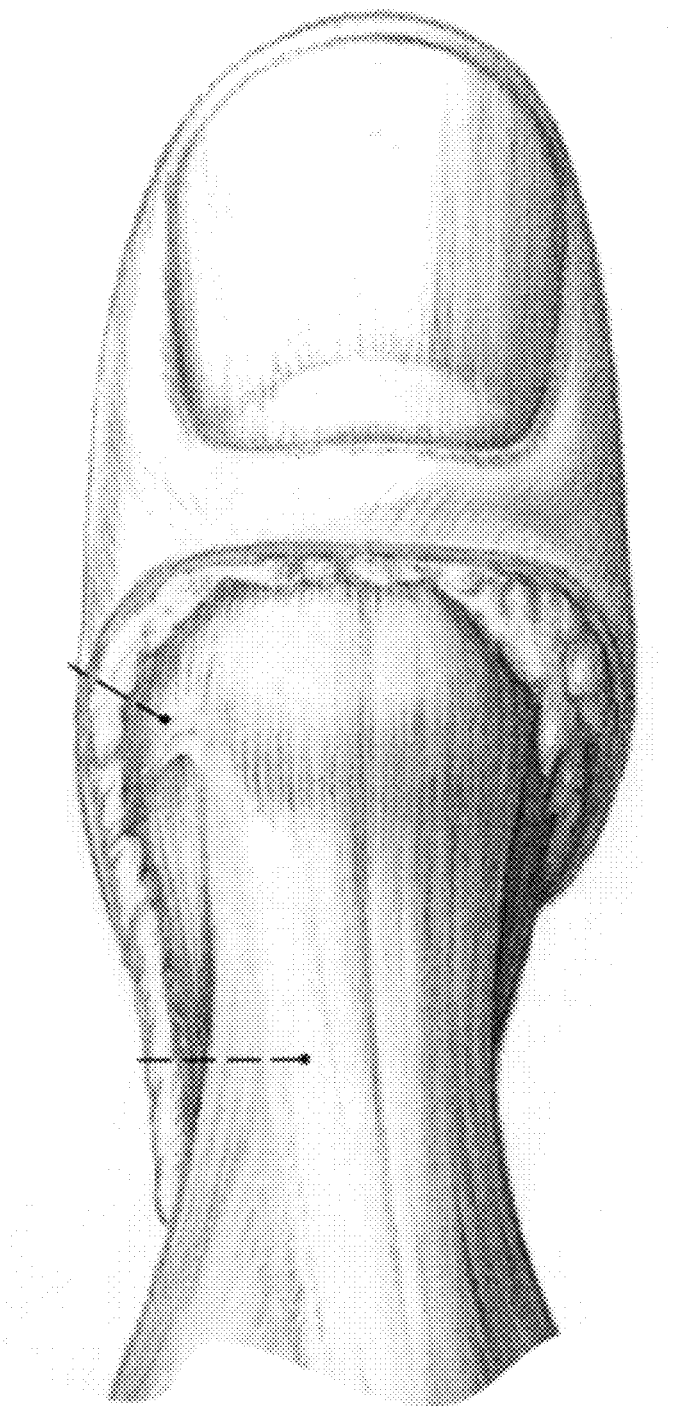
FIG. 1 shows a schematic diagram of an extensor tendon rupture causing mallet finger.
Figure 3:
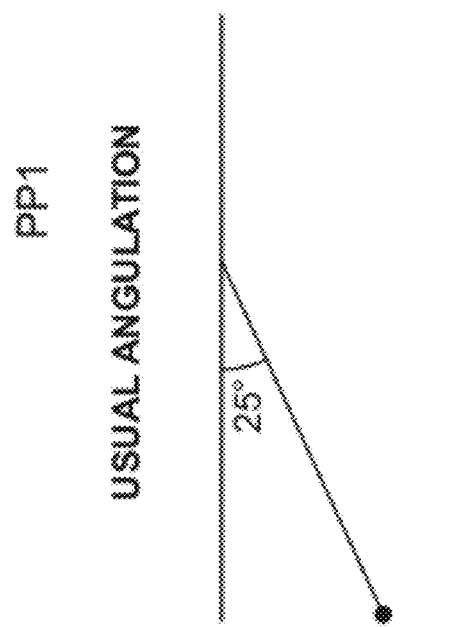
FIG. 3 shows a typical downward angle presentation of mallet finger.
Figure 2:
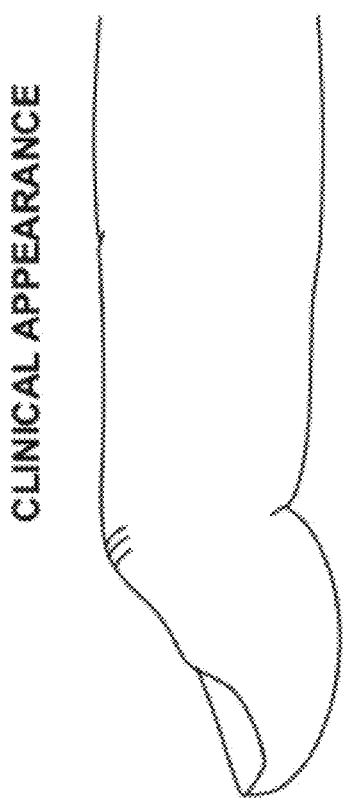
FIG. 2 shows the clinical appearance of mallet finger.
Figure 4:
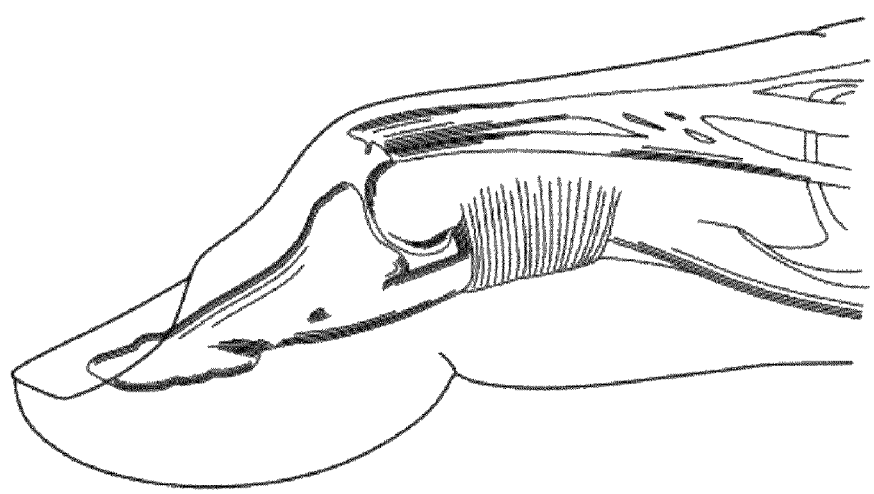
FIG. 4 shows an additional view of a mallet finger injury.
Figure 5:
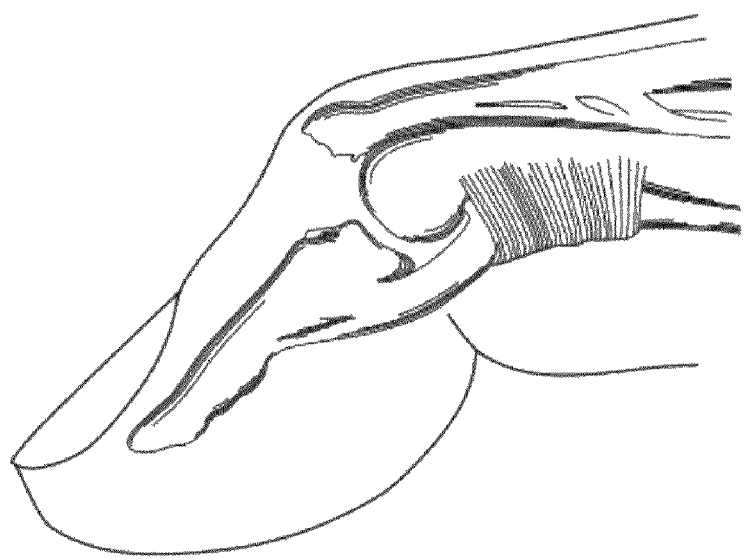
FIG. 5 shows an additional view of a mallet finger injury.
Figure 6:
FIG. 6 shows the detail of one embodiment of a ring having a housing for the dorsal bar which has a hollow path or slot through it. The ring shown is a proximal ring

Each of the rings is configured to be securely attached or connected to the dorsal bar. In a preferred embodiment, each of the rings comprises a portion adapted to receive and engage the dorsal bar (FIG. 6). In a preferred embodiment the dorsal bar slidably engages with the portion of each ring adapted to receive the bar. In a particularly preferred embodiment the dorsal bar and each of the rings are configured such that the dorsal bar slidably engages with each ring in a one-way manner, i.e., once the bar slidably engages with the portion of the ring adapted to receive it, the bar cannot slide back into a prior position.

Figure 11:
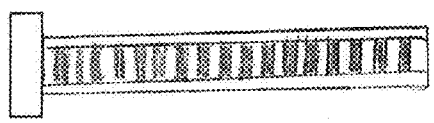
FIG. 11 shows one embodiment of the dorsal bar having transverse striations or an integrated gear rack along its length and a stopping mechanism at one end. In this embodiment the dorsal bar may frictionally engage the portion of the ring adapted to receive it, or may interact with a ratchet contained in the portion of the ring adapted to receive the bar.
Figure 13:
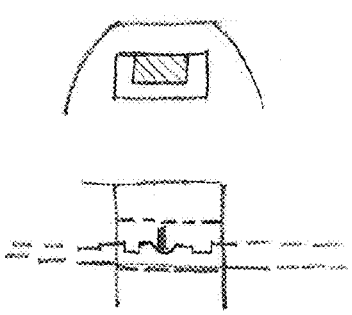
FIG. 13 illustrates the interaction between the dorsal bar embodiment of FIG. 11 and a housing having a slot adapted to receive the dorsal bar. The upper portion of FIG. 13 shows a cross-sectional view of the housing, and the lower portion shows a transparent side perspective of the dorsal bar engaged with the slot in the housing.

In one embodiment the top of the ring has attached thereto a solid portion or housing having a hollow path or slot through it (FIG. 10); the hollow path is suitable to receive the dorsal bar, e.g., the cross section of the dorsal bar is the same shape as the hollow slot. In certain exemplary embodiments the cross section of the dorsal bar is rectangular, and the hollow slot is also rectangular. In other exemplary embodiments the cross section of the dorsal bar is round, and the hollow slot is also round. In some embodiments the hollow slot has an integrated ratchet on the top interior portion (FIG. 13); this ratchet can interact with an integrated gear rack present on some embodiments of the dorsal bar (FIG. 11).

In specific exemplary embodiments the housing attached to each ring is from about $3/16$ inch to about $1/2$ inch high (measured from the insider of the ring at the midpoint of the housing to the top of the ring), $3/16$ inch to about $1/2$ inch long, and about $3/16$ inch to about $1/4$ inch wide. In specific exemplary embodiments the hollow slot is $1/4$ inch wide by $1/8$ inch thick and runs a substantial portion of the length of the solid portion. It should be recognized that the invention is not limited to these parameters, and the measurements of both the housing and the hollow slot of the claimed invention may vary substantially from these exemplary embodiments.

In another embodiment the portion of the ring adapted to receive the dorsal bar is an integral portion of the ring itself. In a preferred embodiment the dorsal surface of the portion adapted to receive the dorsal bar, whether integrated into the ring itself or separately attached, is contoured to reduce sharp edges. This reduces the likelihood that the ring will snag on fabrics or other surfaces or cause injury.

Each of the rings may have a different adaptation for receiving the dorsal bar, but it is preferred that both the proximal and distal rings have the same adaptation for receiving the dorsal bar. Moreover, each ring may be adapted to receive more than one dorsal bar (FIGS. 32-33 and 34-36). For example, each ring may be adapted to receive two dorsal bars (e.g., FIG. 35). In some embodiments the adaptations for receiving the dorsal bar may be located 180 degrees apart on the ring; in such an embodiment the assembled splint would comprise a proximal and distal ring and two dorsal bars, one on each side of the finger to be splinted.

Figure 36:
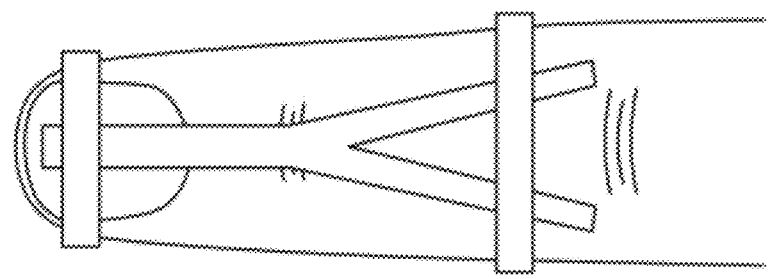
FIG. 36 illustrates a top view of another embodiment of a splint according to the invention. In this embodiment the dorsal bar is a V-shaped bar which engages one of the proximal or distal ring at one position and engages the other of the proximal or distal ring at two positions. It should be understood that modifications of this aspect are also encompassed, i.e., that the dorsal bar(s) merges or bifurcates (trifurcates, etc.) such that different numbers of points of engagement with the proximal and distal rings are encompassed.
Figure 37:
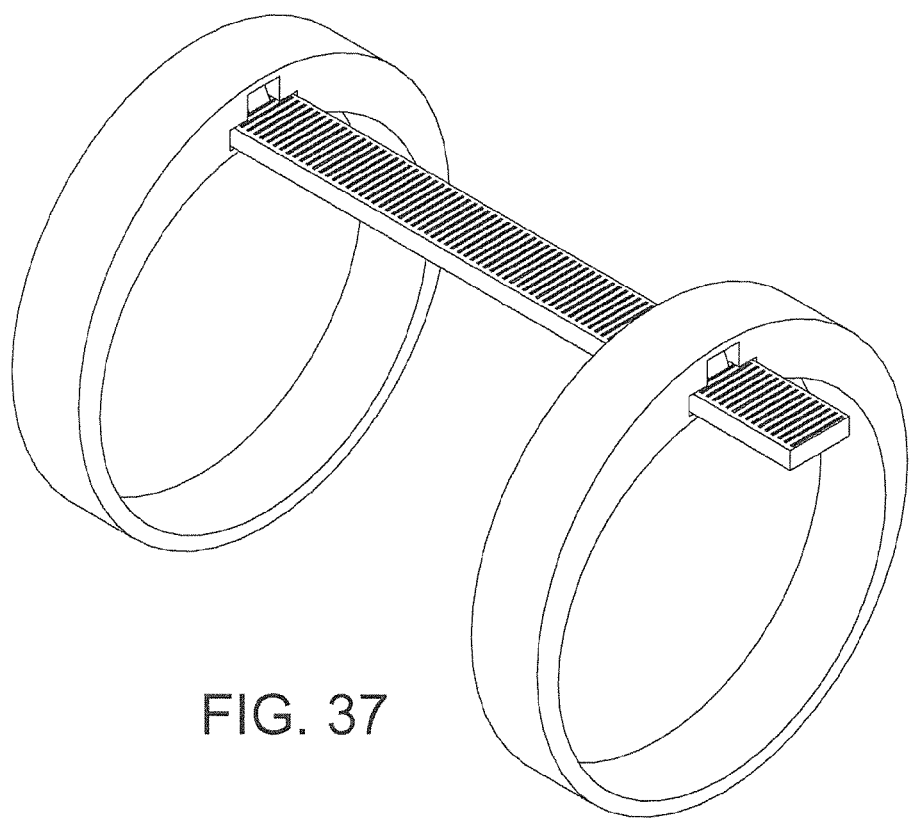
FIG. 37 shows one embodiment of a splint of the invention in which the dorsal bar has transverse striations or an integrated gear rack along its length and a stopping mechanism at one end. In this embodiment the dorsal bar may frictionally engage the portion of the ring adapted to receive it, or may interact with a ratchet contained in the portion of the ring adapted to receive the bar.
Figure 38:
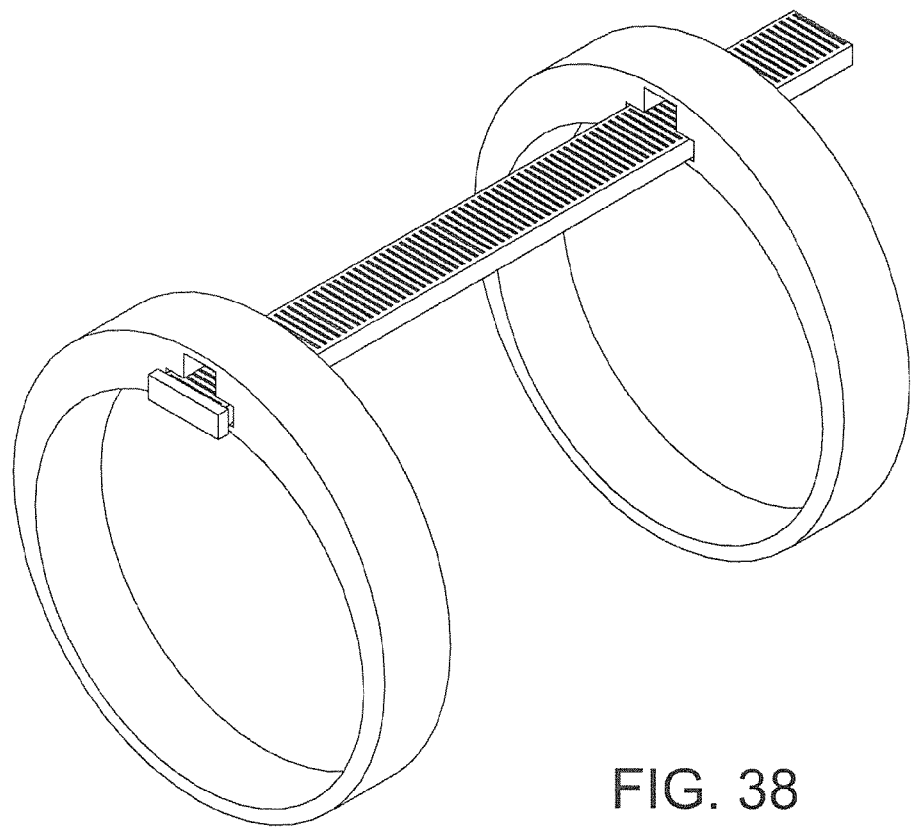
FIG. 38 provides a different perspective of the splint shown in FIG. 37.
Figure 42:
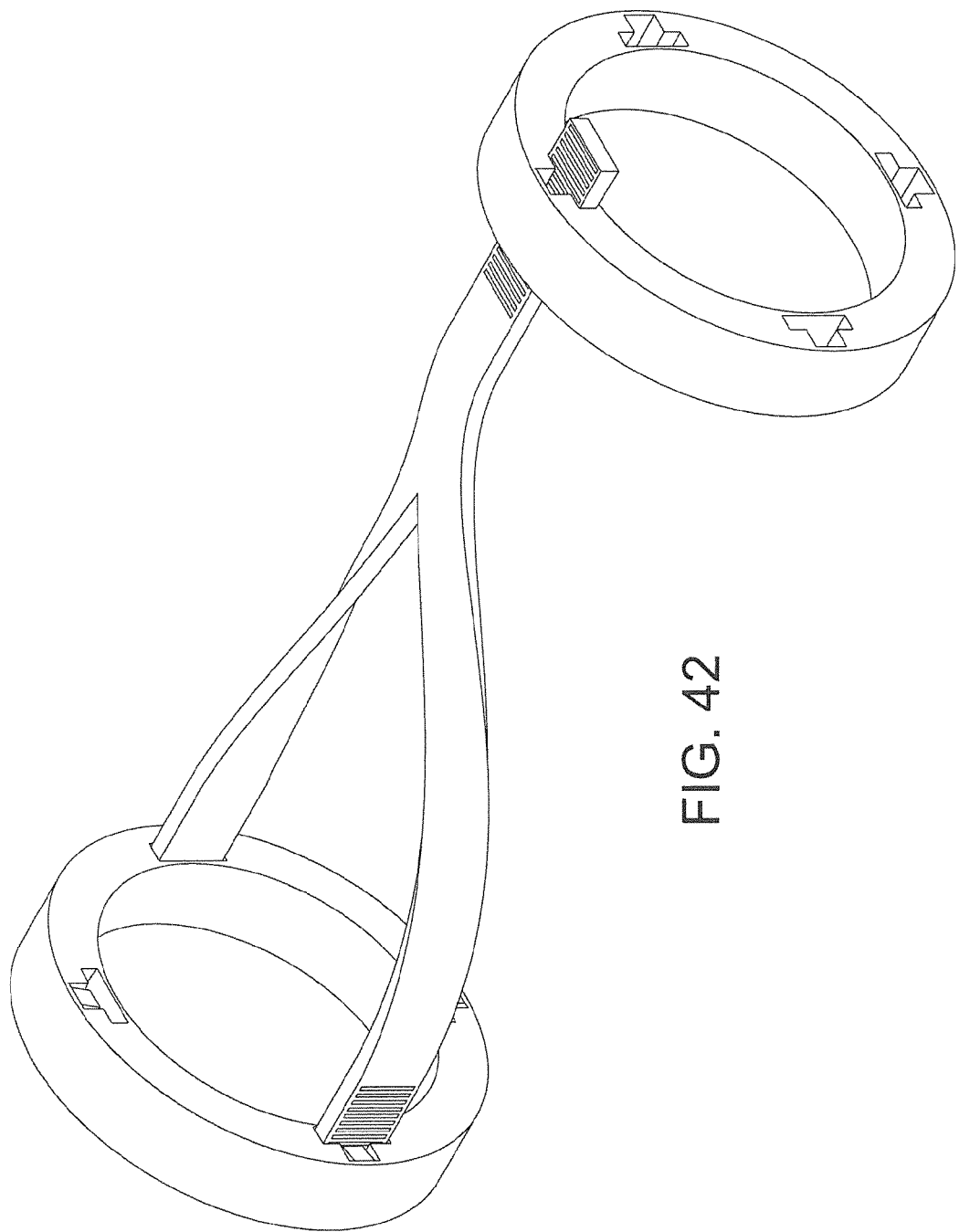
FIG. 42 illustrates one embodiment of a splint of the invention. This embodiment comprises a proximal and a distal ring (each adapted to engage a dorsal bar) along with a bifurcated dorsal bar. Each ring is adapted to engage a dorsal bar (e.g., a bifurcated dorsal bar) at multiple positions and/or to engage multiple dorsal bars. As shown, the portions of the dorsal bar engaged with the rings comprise transverse striations or an integrated gear rack along its length.

The third piece of the splint assembly is the dorsal bar. In a preferred embodiment for treatment of mallet finger injury, the dorsal bar is located on the dorsal side of the finger (i.e., the knuckle side) in the assembled splint. However it should be understood that any positioning of the dorsal bar which immobilizes the finger such that the interphalangeal joint is maintained in a fully extended position is within the scope of the invention. Similarly, multiple dorsal bars may be engaged with the proximal and distal rings as desired. It should also be understood that although this component is referred to as a "bar," other shapes can be utilized in the invention. For example, the dorsal bar may be rod-shaped (having a circular cross section) or have a triangular cross section or can be V-shaped (FIG. 36). The dorsal bar may be straight or may have a moderate curvature, depending upon the desired position of fixation of the joint(s) to be immobilized. The dorsal bar can also be similar in form to a wishbone (FIG. 42). The dorsal bar can be solid or can comprise perforations to allow for airflow, provided that the perforations do not compromise the structural integrity of the dorsal bar and permit undesirable stretching or bending.

The dorsal bar is received by and engaged with both the proximal and distal rings. In one embodiment a surface of the dorsal bar has one or more (e.g., multiple) spaced transverse striations which frictionally engage the portion of the ring adapted to receive the bar (FIG. 11). The striations may be regularly or irregularly spaced. In another embodiment the top surface of the bar comprises an integrated gear rack which engages a ratchet within the portion of the ring adapted to receive the bar (FIGS. 13, 37, 38 and 40); this mechanism of interaction is akin to the operation of a cable zip tie.

Figure 12:
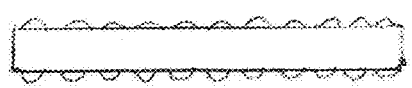
FIG. 12 shows one embodiment of the dorsal bar having bumps or beads arrayed along the length of the bar which can frictionally engage the portion of the ring adapted to receive it.
Figure 14:
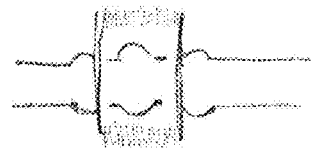
FIG. 14 illustrates the interaction between the dorsal bar embodiment of FIG. 12 and a housing having a slot adapted to receive the dorsal bar. The lower portion of FIG. 13 shows a cross-sectional view of the housing, and the upper portion shows a transparent side perspective of the dorsal bar engaged with the slot in the housing.
Figure 39:
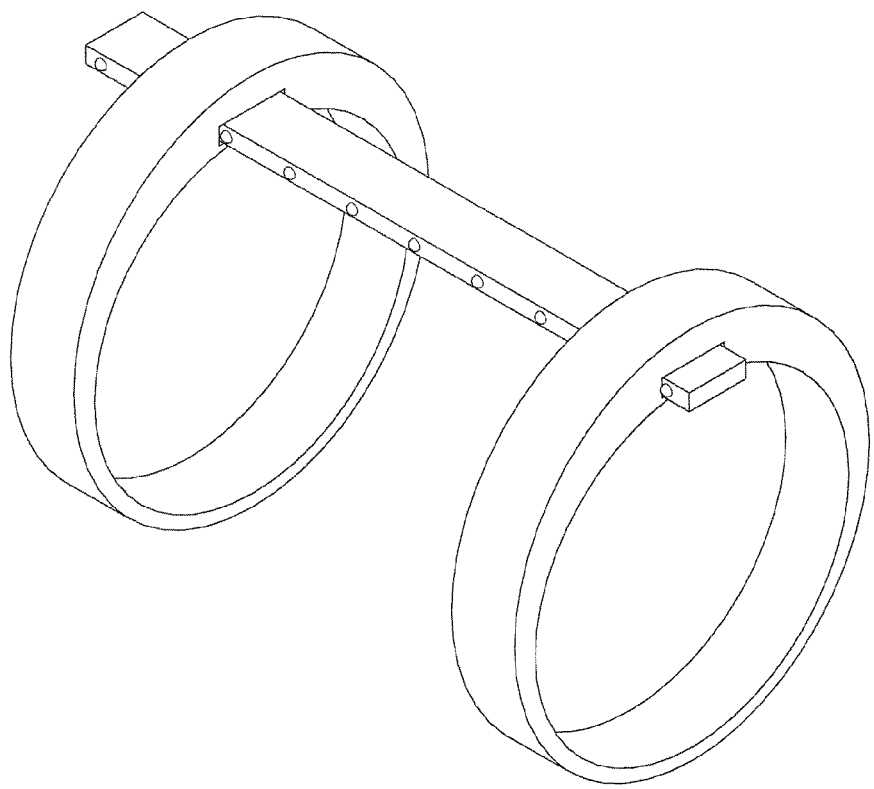
FIG. 39 illustrates one embodiment of a splint of the invention utilizing a dorsal bar having bumps or beads arrayed along the length of the bar which can frictionally engage the portion of the proximal and distal rings adapted to receive it.
Figure 40:
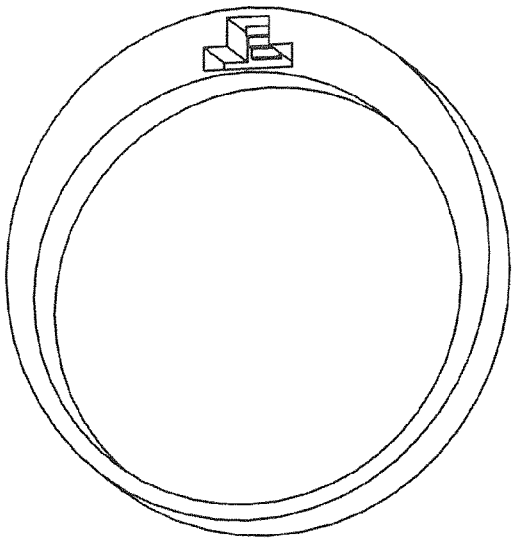
FIG. 40 shows a ring with a housing having a ratchet element contained on the upper portion of the housing's slot.
Figure 41:
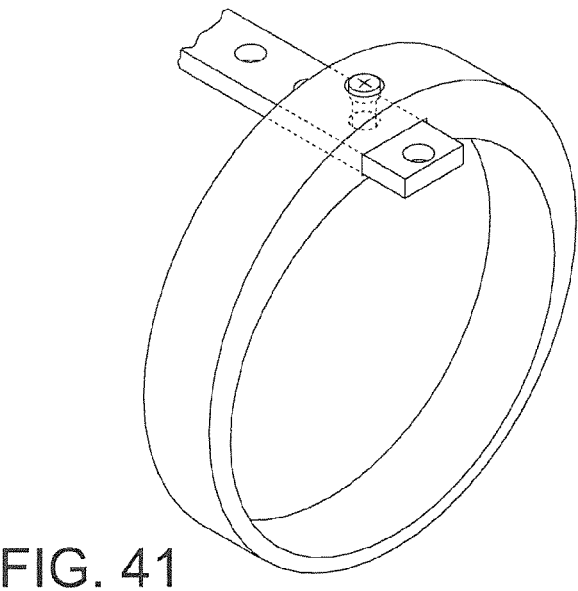
FIG. 41 illustrates one embodiment of the dorsal bar engaged with a proximal or distal ring. In this embodiment a screw or other fastener passes through a hole or slot in the ring and fixedly connects (e.g., by screwing) to the dorsal bar (e.g., to a hole or slot in the dorsal bar) positioned within the slot in the ring's housing.

In another embodiment one or more edges of the dorsal bar comprise one or more bumps or beads which frictionally engage the portion of the ring adapted to receive the bar (FIGS. 12, 14 and 39). The bumps or beads may also be spring-loaded such that they springably retract upon contact with a surface (via spring compression) and return to their original position upon, e.g., seating in a receptacle within the portion of the ring receiving the dorsal bar.

In another embodiment the dorsal bar comprises one or more holes or slots capable of engaging (or being engaged by) a connector located in a portion of a ring adapted to engage the dorsal bar (FIGS. 16-18 and 41). In this embodiment the ring also has a hole or slot, and a connector or fastener passes through a hole or slot in the ring and fixedly connects (to the dorsal bar (e.g., to a hole or slot in the dorsal bar). For example, the connector can be a screw, a rivet, or a snap.

Other mechanisms of interaction and engagement between the dorsal bar and the portion of a ring adapted to receive and engage it will be apparent to the skilled artisan and are encompassed by the invention.

In preferred embodiments the dorsal bar has a stopping mechanism at one end to prevent the bar from passing completely through the portion of the ring adapted to receive the bar (FIG. 15). This stopping mechanism is sized such that it will not pass through the portion of the ring adapted to receive the bar, thus acting as a brake or anchor. The stopping mechanism can be, for example, a square or rectangular portion (e.g., metal, plastic, etc.) that is fixedly attached to one end of the dorsal bar (e.g., formed integrally with the bar or attached to the bar). In one embodiment the stopping mechanism is laterally larger than the bar by, e.g., $1/8^{th}$ inch. If the stopping mechanism is attached distally, the correct position of the distal phalanx can be ascertained visually and the bar set at this position by adjusting the position of the rod on the proximal ring. The rod could then be trimmed at this length, perhaps leaving a minimal amount in case further adjustments are necessary.

In one embodiment the dorsal bar is, for example, 2.5 inches long, $1/4$ inch wide, and $1/16$ inch thick. These parameters are not limiting, however, as the proper length, width, and thickness of the dorsal bar will depend on the material from which it is formed and the size of the finger to be splinted. The dorsal bar should be sufficiently rigid to prevent undesirable stretching or bending under normal conditions during the duration of use. Undesirable stretching or bending is stretching or bending which permits the interphalangeal joint to assume a position short of full extension. For example, the dorsal bar can be formed of plastic or other polymer, metal (e.g., stainless steel), glass, and the like. In a preferred embodiment the dorsal bar is formed of a water-resistant or waterproof material. In a preferred embodiment the dorsal bar is formed of a non-reactive material.

Figure 43:
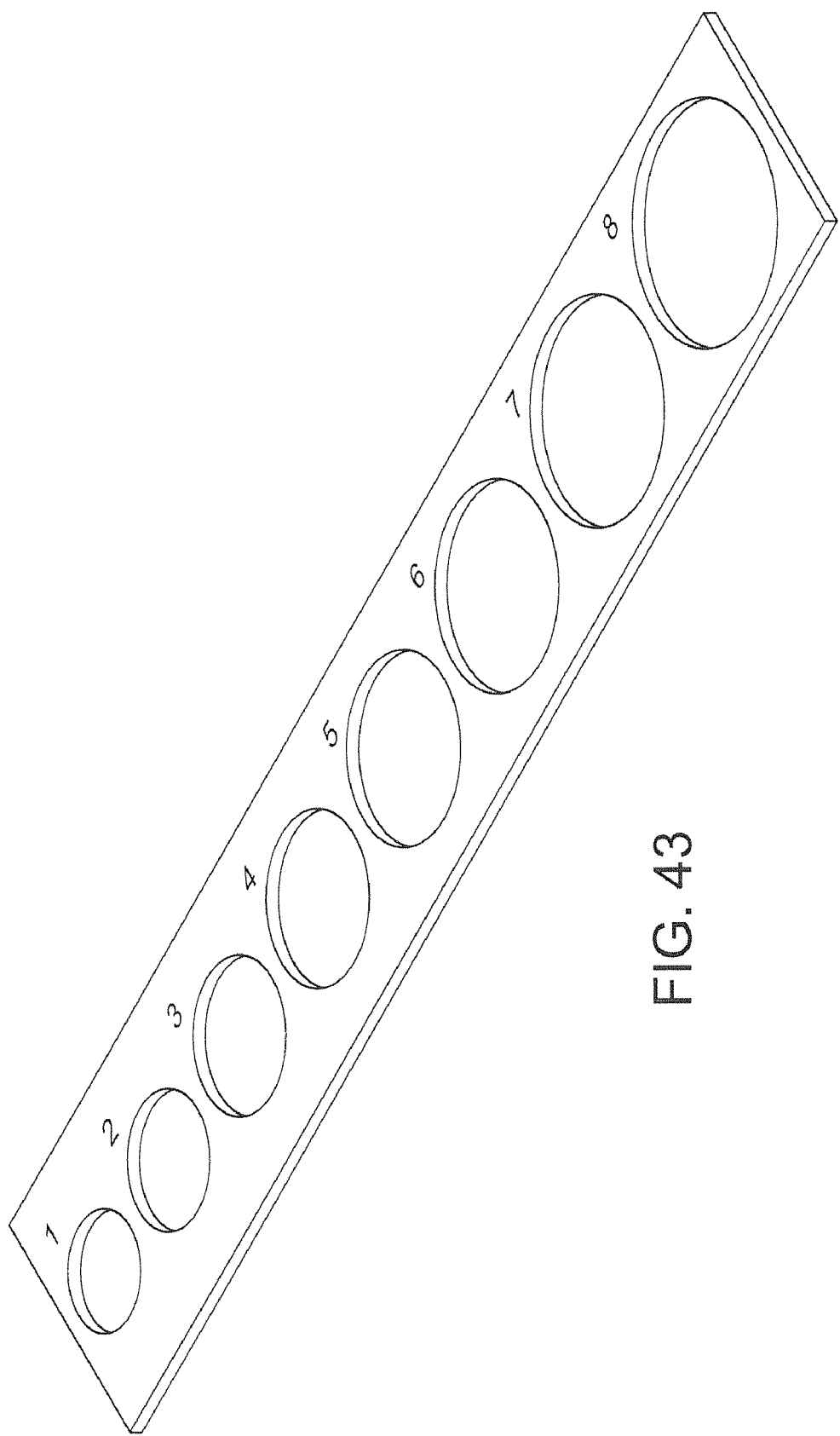
FIG. 43 illustrates an exemplary ring sizing apparatus to aid in selecting proximal and/or distal rings of appropriate size for a patient.

Accordingly the invention further comprises a method of splinting a finger utilizing the splint assembly of the invention. The circumference of the finger may be measure by a measuring device (e.g., a device as shown in FIG. 43) at two levels: the middle of the middle phalanx and the middle of the distal phalanx. Based on this measurement, proximal and distal rings of appropriate size are selected. Alternatively proximal and distal rings can be selected by testing them in a trial-and-error fashion on the finger to be splinted.

In one embodiment the proximal ring is placed on the finger, and the distal ring is placed on the finger and adhered to the finger nail. Preferably the distal ring is adhered just distal to the nail fold. Any suitable adhesive can be used to secure the distal ring to the fingernail. For example, a physiologically compatible or medical grade adhesive (e.g., an epoxy glue) can be used. In preferred embodiments the adhesive is sufficient to adhere the distal ring to the nail for the duration of wear. In preferred embodiments the adhesive is capable of being removed at the end of wear without undue damage to the fingernail. In a particular embodiment a fast setting adhesive is used which provides sufficient time for adjustment prior to setting but which sets relatively quickly (e.g., 1-3 minutes, 2-3 minutes, 3-5 minutes, etc.).

The dorsal bar is engaged by both the distal and proximal rings to produce an appropriate level of tension (FIGS. 19-25). In a particularly preferred embodiment the dorsal bar and each of the rings are configured such that the dorsal bar slidably engages with each ring in a one-way manner, i.e., once the bar slidably engages with the portion of the ring adapted to receive it, the bar cannot slide back into a prior position. In this embodiment the dorsal bar is passed through one ring in the permitted direction until its progress is impeded by a stopping mechanism. The dorsal bar is then passed through the other ring in the permitted direction until the finger is pulled into the desired position, i.e., the desired level of tension is attained. Excess length of dorsal bar which has passed through the second ring may optionally be trimmed to produce a tidier and more discrete splint assembly. In some embodiments the assembled splint can be slightly adjusted after application (e.g., by permitting slight adjustability of the bar vis-à-vis the proximal ring).

Figure 19:
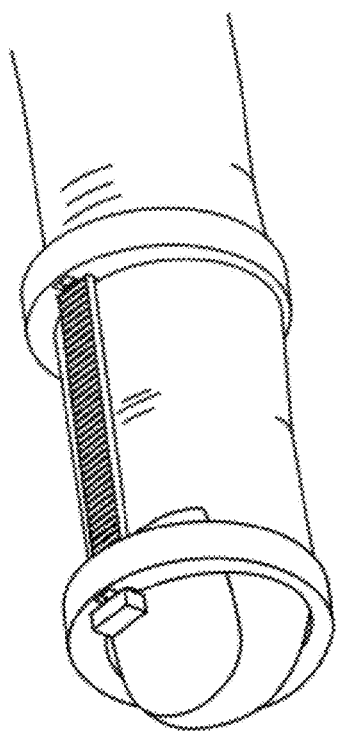
FIG. 19 illustrates a skewed top view of one embodiment of an assembled splint of the invention comprising a distal ring, a proximal ring, and a dorsal bar. In this embodiment the portion adapted for receiving the dorsal bar is an integral part of the ring. The dorsal surface can be contoured as shown to reduce sharp edges and thus reduce the likelihood that the ring will snag on fabrics or other surfaces or cause injury.
Figure 21:
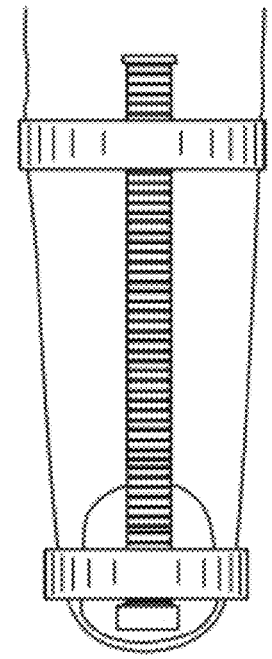
FIG. 21 shows a top view of one embodiment of an assembled splint of the invention comprising a distal ring, a proximal ring, and a dorsal bar.
Figure 20:
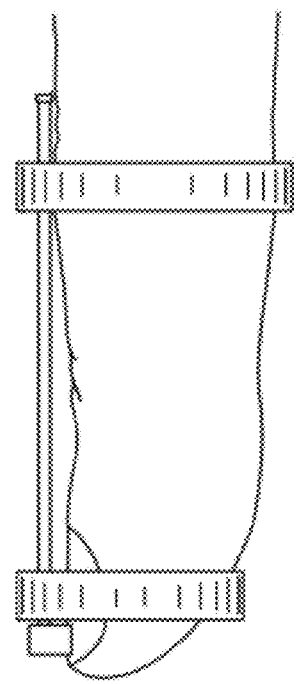
FIG. 20 illustrates a side view of one embodiment of an assembled splint of the invention comprising a distal ring, a proximal ring, and a dorsal bar.
Figure 22:
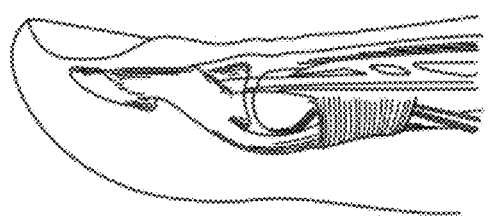
FIG. 22 shows a top view of a mallet finger injury properly positioned for splinting.
Figure 23:
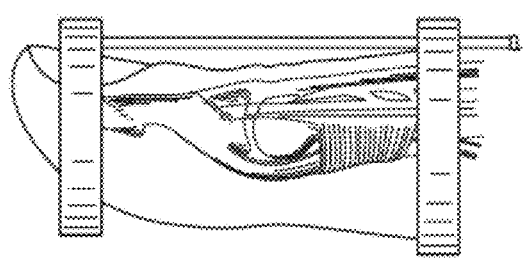
FIG. 23 shows a side view of a mallet finger injury properly positioned for splinting.
Figure 24:
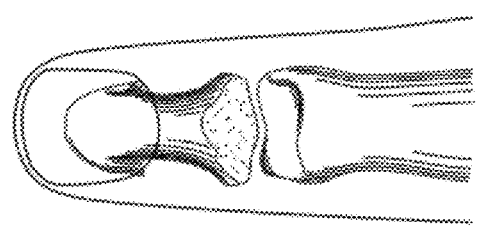
FIG. 24 shows a top view of one embodiment of a splint of the invention holding a mallet finger injury in proper position for healing.
Figure 25:
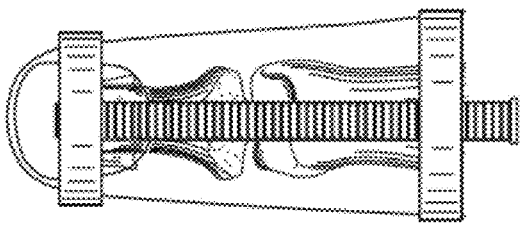
FIG. 25 shows a side view of one embodiment of a splint of the invention holding a mallet finger injury in proper position for healing.
Figure 26:
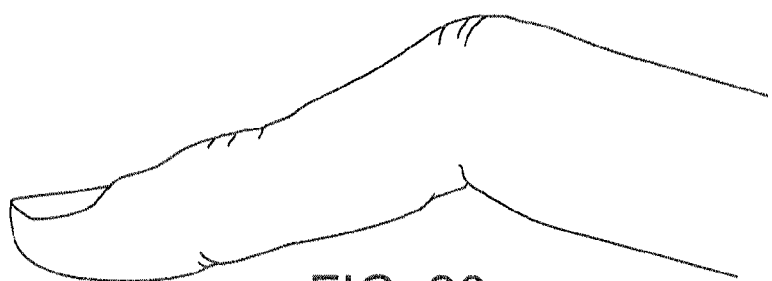
FIG. 26 shows a finger having an injury causing forced flexion at the second interphalangeal joint.
Figure 27:
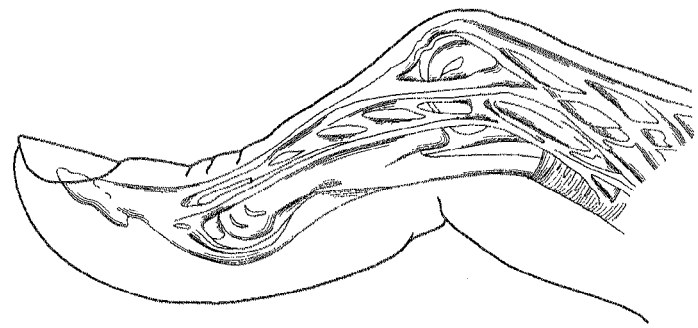
FIG. 27 shows a side internal view of a finger having an injury causing forced flexion at the second interphalangeal joint.
Figure 28:
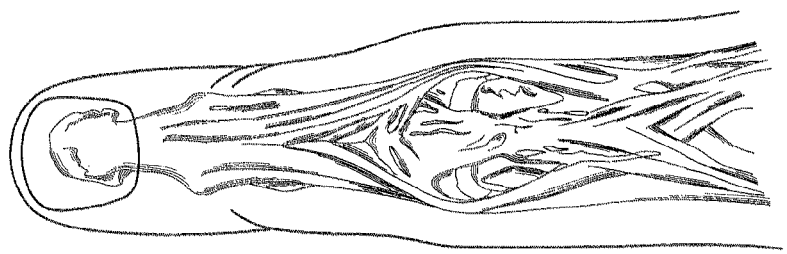
FIG. 28 shows a top internal view of a finger having an injury causing forced flexion at the second interphalangeal joint.
Figure 29:
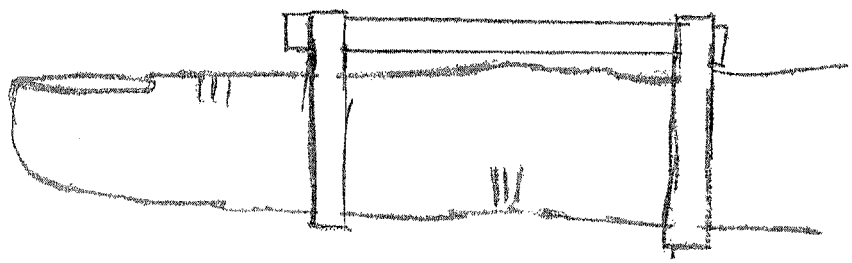
FIG. 29 shows a side view of one embodiment of a splint of the invention holding a finger having the injury shown in FIGS. 26-28 in proper position for healing. In this embodiment the distal ring is not affixed to the finger nail. The proximal and/or distal ring may be transiently affixed to the skin of the finger to prevent or reduce rotation of the assembly around the finger.
Figure 34:
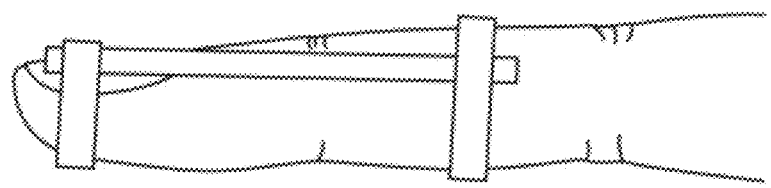
FIG. 34 illustrates a side view of another embodiment of a splint according to the invention. In this embodiment the dorsal bar is engaged by the proximal and distal rings diagonally.
Figure 35:
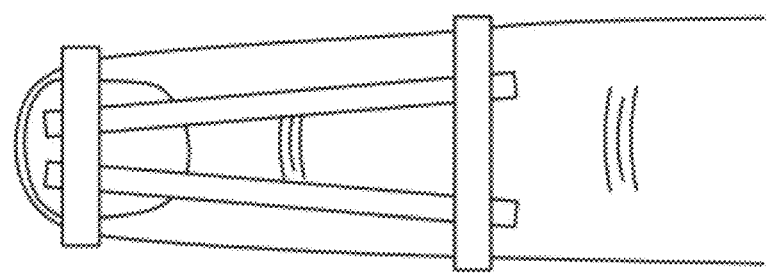
FIG. 35 illustrates a top view of another embodiment of a splint according to the invention. In this embodiment the proximal and distal rings are engaged with multiple dorsal bars diagonally positioned.

The order of assembly of the splint is not critical; all that is required is that the proximal ring is placed on the finger before the distal ring. In one embodiment the dorsal bar is passed through the distal ring either before or after the ring has been adhered to the fingernail and is subsequently passed through the proximal ring (which has already been positioned on the finger). In another such embodiment the dorsal bar is passed through the proximal ring before or after it has been positioned on the finger and is subsequently passed through the distal ring. The splint assembly may be loosely assembled prior to placing either ring on the finger, and the bar shortened to produce the proper tension level after the rings are placed on the finger and the distal ring is adhered to the fingernail. The finished splint assembly positioned on the finger is shown in FIGS. 19-20.

Figure 44:
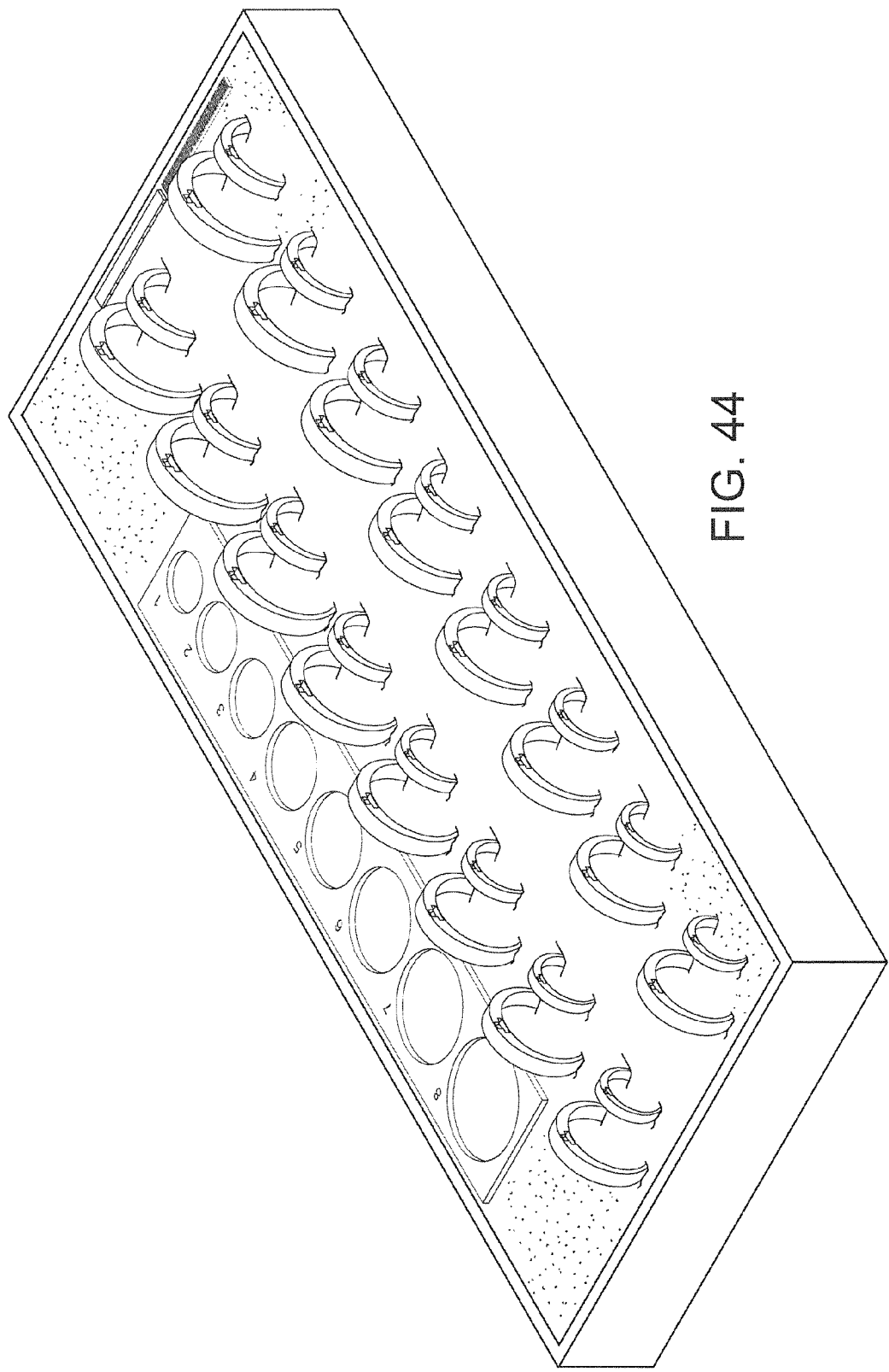
FIG. 44 illustrates an exemplary embodiment of a kit of the invention. In this embodiment the kit comprises a ring sizing apparatus, multiple proximal and distal rings in graduated sizes, and multiple dorsal bars for use with the proximal and distal rings. In this embodiment the elements are packaged together and sold in a box or tray for containing and displaying the elements.

The invention further provides a kit comprising components of the splint assembly (e.g., comprising one or more distal rings, one or more proximal rings and one or more dorsal bars), optionally packaged with one or more related items such as one or more sizers, a tool for trimming the dorsal bar, suitable adhesive for adhering the distal ring to the nail, suitable adhesive solvent, and/or instructions for use. The kit may, for example, contain distal rings of multiple sizes, proximal rings of multiple sizes, and/or dorsal bars of multiple sizes (FIG. 44). Kits of the invention may contain the components separated from (not connected to) one another; in other embodiments the splint assembly can be partially assembled (e.g., a dorsal bar may be connected to one or more of the proximal and distal rings). In a preferred embodiment the dorsal bars included in the kit are adapted for use with the rings included in the same kit, i.e., are adapted to engage the rings included in the same kit. Other kits of the invention may contain only one type of component of the splint (i.e., may contain only rings for use in the splint, may contain only distal rings for use in a splint, may contain only proximal rings for use in a splint, may contain only dorsal bars for use in a splint, etc.) or may contain two or more types of component of the splint.

What is claimed is:

1. A splint for splinting a digit comprising:
a dorsal bar having two ends;
a distal ring comprising one or more portions adapted to securely connect to one end of the dorsal bar; and
a proximal ring comprising one or more portions adapted to securely connect to the other end of the dorsal bar,
wherein the dorsal bar is securely connected to both the distal and proximal rings such that one or more joints of a digit to which the splint is applied is maintained in an extended position, and wherein one or more portions of the distal ring, the proximal ring, or both the distal and proximal rings adapted to securely connect to the dorsal bar comprises a housing having a hollow slot therethrough suitable to receive the dorsal bar.

2. A splint for splinting a digit comprising:
a dorsal bar having two ends;
a distal ring comprising one or more portions adapted to securely connect to one end of the dorsal bar; and
a proximal ring comprising one or more portions adapted to securely connect to the other end of the dorsal bar,
wherein the dorsal bar is securely connected to both the distal and proximal rings such that one or more joints of a digit to which the splint is applied is maintained in an extended position; wherein one or more portions of the distal ring, the proximal ring, or both the distal and proximal rings adapted to securely connect to the dorsal bar are adapted to engage the dorsal bar and comprise a ratchet capable of engaging the dorsal bar; wherein one or more portions of the distal ring, the proximal ring, or both the distal and proximal rings adapted to securely connect to the dorsal bar comprise a ratchet capable of engaging the dorsal bar; and wherein the dorsal bar comprises an integrated gear rack which engages the ratchet.

3. A splint for splinting a digit comprising:
a dorsal bar having two ends;
a distal ring comprising one or more portions adapted to securely connect to one end of the dorsal bar; and
a proximal ring comprising one or more portions adapted to securely connect to the other end of the dorsal bar,
wherein the dorsal bar is securely connected to both the distal and proximal rings such that one or more joints of a digit to which the splint is applied is maintained in an extended position, and wherein the dorsal bar slidably engages with both the proximal and distal rings.

4. A splint according to claim 3 wherein the dorsal bar slidably engages with both the proximal and distal rings in only one direction.

5. A splint for splinting a digit comprising:
a dorsal bar having two ends;
a distal ring comprising one or more portions adapted to securely connect to one end of the dorsal bar; and
a proximal ring comprising one or more portions adapted to securely connect to the other end of the dorsal bar,
wherein the dorsal bar is securely connected to both the distal and proximal rings such that one or more joints of a digit to which the splint is applied is maintained in an extended position, wherein the dorsal bar comprises a stopping mechanism.

\* \* \* \* \*